US011136284B2

(12) United States Patent
Kim et al.

(10) Patent No.: US 11,136,284 B2
(45) Date of Patent: *Oct. 5, 2021

(54) PROCESS FOR HYDROGENATION OF PHTHALATE COMPOUND

(71) Applicant: Hanwha Solutions Corporation, Seoul (KR)

(72) Inventors: Hyo Suk Kim, Daejeon (KR); Ki Taeg Jung, Daejeon (KR); Seong Min Park, Seoul (KR); Kyoung Il Lee, Daejeon (KR); Hye Won Lee, Daejeon (KR); Jae Heum Jung, Busan (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/763,665

(22) PCT Filed: Nov. 1, 2018

(86) PCT No.: PCT/KR2018/013195
§ 371 (c)(1),
(2) Date: May 13, 2020

(87) PCT Pub. No.: WO2019/107771
PCT Pub. Date: Jun. 6, 2019

(65) Prior Publication Data
US 2020/0361846 A1    Nov. 19, 2020

(30) Foreign Application Priority Data
Nov. 29, 2017  (KR) .................. 10-2017-0161950

(51) Int. Cl.
*C07C 51/36* (2006.01)
*B01J 23/46* (2006.01)
*C08K 5/101* (2006.01)

(52) U.S. Cl.
CPC ............. *C07C 51/36* (2013.01); *B01J 23/462* (2013.01); *C08K 5/101* (2013.01)

(58) Field of Classification Search
CPC ....... C07C 67/303; C07C 69/75; C07C 51/36; C08L 101/00; C08K 5/12
See application file for complete search history.

(56) References Cited

U.S. PATENT DOCUMENTS

| 2,743,302 | A | * | 4/1956 | Gwynn | .................... C07C 29/76 568/882 |
| 6,437,170 | B1 | * | 8/2002 | Thil | ........................ C07C 69/44 560/76 |
| 7,361,714 | B2 | * | 4/2008 | Grass | ..................... B01J 23/462 525/338 |
| 7,435,848 | B2 | * | 10/2008 | Grass | .................... C07C 67/303 560/116 |
| 7,683,204 | B2 | | 3/2010 | Buschken et al. | |
| 8,946,467 | B2 | * | 2/2015 | Reine | .................... C07C 67/303 560/127 |
| 2006/0161017 | A1 | * | 7/2006 | Grass | .................... C07C 67/303 562/509 |
| 2012/0296111 | A1 | * | 11/2012 | Konigsmann | .......... B01J 35/008 560/127 |
| 2018/0015450 | A1 | | 1/2018 | Jung et al. | |
| 2019/0048167 | A1 | * | 2/2019 | Kim | ........................ C07C 67/08 |
| 2020/0299222 | A1 | * | 9/2020 | Lee | ........................ C08K 5/101 |

FOREIGN PATENT DOCUMENTS

| CN | 103130648 A | * | 6/2013 |
| CN | 105037161 A | * | 11/2015 |
| EP | 3085686 | | 10/2016 |
| KR | 10-2012-0092197 | | 8/2012 |
| KR | 10-1556340 | | 6/2015 |
| KR | 101556340 B1 | * | 9/2015 |
| KR | 10-2016-0118010 | | 10/2016 |
| KR | 10-1797220 | | 3/2017 |

OTHER PUBLICATIONS

Henryetai, Industrial & Engineering Chemistry Process Design and Development, Scale Up of Pilot Plant Data for Catalytic Hydroprocessing, 1973, 12(3), pp. 328-334. (Year: 1973).*
D. Hlushkou et al., Journal of Chromatography A, 70-85 (2006) (Year: 2006).*
P. de Souza Mendes, 147 Journal of Non-Newtonian Fluid Mechanics, 109-116 (2007) (Year: 2007).*
R. Pfeffer et al., A.ICh.E. Journal (1964) (Year: 1964).*
KIPO, PCT Search Report & Written Opinion of PCT/KR2018/013195 dated Apr. 18, 2019.
EPO, Extended European Search Report of EP 18882595.4 dated Aug. 12, 2021.

* cited by examiner

*Primary Examiner* — Alexander R Pagano
(74) *Attorney, Agent, or Firm* — Lex IP Meister, PLLC

(57) ABSTRACT

Provided is a hydrogenation method of a phthalate compound. According to the present invention, stereoselectivity of the hydrogenation reaction may be increased, and thus the content of a cis isomer in a product may be increased. As a result, quality of the hydrogenation product as a plasticizer may be improved.

4 Claims, 1 Drawing Sheet

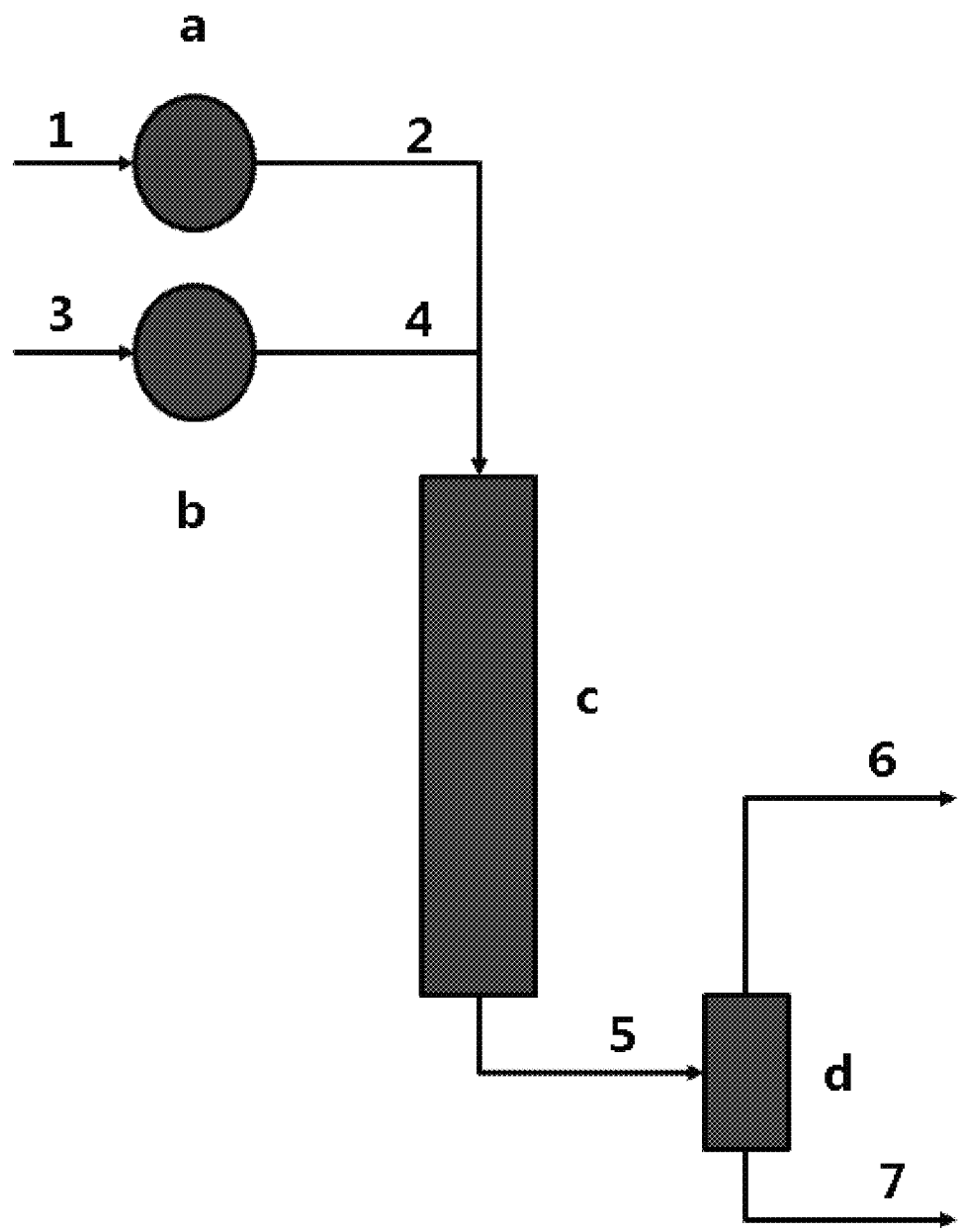

PROCESS FOR HYDROGENATION OF PHTHALATE COMPOUND

CROSS-REFERENCE TO RELATED APPLICATION

The present application is based on, and claims priority from, Korean Patent Application No. 10-2017-0161950, filed on Nov. 29, 2017, the disclosure of which is hereby incorporated by reference herein in its entirety.

TECHNICAL FIELD

The present invention relates to a hydrogenation method of a phthalate compound. Particularly, the present invention relates to a hydrogenation method of a phthalate compound, the method capable of increasing the content of a cis-isomer in a hydrogenation product by increasing stereoselectivity of the reaction.

BACKGROUND ART

Phthalate-based compounds are materials widely used as plasticizers for plastics, particularly, polyvinyl chloride (PVC). For example, phthalate-based compounds may be used in a wide variety of applications such as electrical and electronic products, medicines, paint pigments, lubricants, binders, surfactants, adhesives, tiles, food containers, package materials, etc.

However, since some of the phthalate compounds have been known to be materials causing environmental pollution and human endocrinal disruption problems, restrictions on use thereof have been tightened in advanced countries such as Europe, the US, etc. Particularly, among phthalate-based plasticizers, some products such as di(2-ethylhexyl) phthalate (DEHP), butyl benzyl phthalate (BBP), and di-n-butyl phthalate (DBP) are suspected to be environmental hormones, that is, endocrine disruptors inhibiting or disrupting hormone actions in the human body, such that there is a trend toward regulation on these products.

For this reason, efforts have been made to develop an eco-friendly plasticizer free from debate in terms of environmental hormones while having performance equal to that of the existing plasticizers. As one of the efforts, there is a method of using a compound which is prepared by hydrogenation of a benzene ring included in a phthalate compound.

As a hydrogenation reaction of an aromatic compound such as a benzene ring, a method of using a catalyst in which a transition metal such as ruthenium is contained as an active ingredient on a support has been known.

However, the transition metal catalyst has a problem in that its activity rapidly decreases while the reaction proceeds, resulting in a yield reduction. Accordingly, efforts have been continued to solve the problems of the hydrogenation reaction for improvement of productivity and economic efficiency of the process. For example, Korean Patent No. 1556340 discloses a hydrogenation method of reacting a phthalate compound with hydrogen in the presence of a hydrogenation catalyst and an alcohol, whereby performance and life-time of the catalyst are improved.

Meanwhile, the hydrogenation reaction entails side reactions. As the content of by-products increases, the manufactured product becomes acidic. If an acid value of the product exceeds a certain level, an odor is produced and purity decreases, resulting in generation of quality problems as a plasticizer. Moreover, the by-products also lower activity of the hydrogenation catalyst, and accordingly, there is a need for a novel hydrogenation method of a phthalate compound capable of suppressing generation of by-products in order to improve productivity and economic efficiency of the process and to improve quality of the product.

PRIOR ART DOCUMENT

Patent Document 1: Korean Patent No. 1556340, "Hydrogenation method of phthalate compound"

DISCLOSURE

Technical Problem

The present invention has been made to solve the above problems, and an object of the present invention is to provide a hydrogenation method of a phthalate compound, the method being capable of increasing the content of a cis-isomer in a hydrogenation product.

Technical Solution

To achieve the above object, there is provided a hydrogenation method of a phthalate compound, the method including the steps of introducing a gas-phase raw material including hydrogen and a liquid-phase raw material including the phthalate compound into a reactor and allowing a reaction of the hydrogen and the phthalate compound in the presence of a hydrogenation catalyst, wherein the Reynold's number of the liquid-phase raw material is 1 to 100, and the content of a cis isomer in a hydrogenation product separated after the reaction is 70% or more.

The amount of hydrogen introduced into the reactor may be 3 mol to 300 mol with respect to 1 mol of the phthalate compound.

The phthalate compound may be one or more selected from the group consisting of phthalate, terephthalate, isophthalate, and carboxylic acid compounds thereof.

The gas-phase raw material may be fed into an upper portion or a lower portion of the reactor, and the liquid-phase raw material may be fed into an upper portion of the reactor.

The active ingredient of the hydrogenation catalyst may be one or more selected from the group consisting of ruthenium (Ru), rhodium (Rh), palladium (Pd), and platinum (Pt).

The hydrogenation catalyst may include 3% by weight or less of the catalyst active ingredient with respect to 100% by weight of a support.

Further, there is provided a hydrogenated phthalate or terephthalate compound prepared by the above method.

The hydrogenated phthalate or terephthalate compound may be used as a plasticizer.

Furthermore, there is provided a resin composition including the plasticizer; and a resin selected from ethylene vinyl acetate, polyethylene, polypropylene, polyvinyl chloride, polystyrene, polyurethane, polybutadiene, silicone, thermoplastic elastomers, and copolymers thereof.

Effect of the Invention

According to a hydrogenation method of a phthalate compound of the present invention, stereoselectivity of the hydrogenation reaction may be increased, and thus the content of a cis isomer in a product may be increased. As a result, quality of the hydrogenation product as a plasticizer may be improved.

BRIEF DESCRIPTION OF DRAWINGS

The drawing is a schematic illustration of a hydrogenation reaction apparatus used in a hydrogenation method of the present invention.

BEST MODE FOR CARRYING OUT THE INVENTION

The present invention may be variously modified and have various embodiments, and specific embodiments will be exemplified and described in detail. However, the present invention is not limited to the exemplary embodiments described herein, but all of the modifications, equivalents, and substitutions within the spirit and scope of the present invention are also included in the present invention. Further, when it is determined that the detailed description of the known art related to the present invention may obscure the gist of the present invention, the detailed description thereof will be omitted.

In addition, terms including an ordinal number such as first, second, or the like, to be used below may be used to describe various components. However, these components are not limited to these terms. The terms are only used to differentiate one component from other components. For example, the 'first' component may be named the 'second' component and the 'second' component may also be similarly named the 'first' component, without departing from the scope of the present invention.

Singular forms are intended to include plural forms unless the context clearly indicates otherwise. Terms such as "include", "have", and the like, used in the present specification will imply the existence of stated features, numbers, steps, operations, configuration elements, components, or a combination thereof, but do not preclude the presence or addition of one or more other features, numbers, steps, operations, configuration elements, components, or a combination thereof.

Hereinafter, a hydrogenation method of a phthalate compound of the present invention will be described in detail with reference to drawings.

According to a preferred embodiment of the present invention, provided is a hydrogenation method of a phthalate compound, the method including the steps of introducing a gas-phase raw material including hydrogen and a liquid-phase raw material including the phthalate compound into a reactor and allowing a reaction of the hydrogen and the phthalate compound in the presence of a hydrogenation catalyst, wherein the Reynold's number of the liquid-phase raw material is 1 to 100, and the content of a cis isomer in a hydrogenation product separated after the reaction is 70% or more.

In the present invention, stereoselectivity of the hydrogenation reaction of the phthalate compound may be increased by operating while controlling the Reynold's number of the liquid-phase raw material within a specific numerical range. In other words, according to the present invention, the hydrogenation product has a high cis isomer content of 70% or more, and such the hydrogenation product may exhibit excellent plasticizing efficiency for PVC resins, a high absorption rate, and product transparency after solidification, and has excellent properties as a plastic plasticizer due to low leaching from the product surface even after long-term use thereof. Therefore, the present invention may be applied to the production of a high-quality plasticizer.

A reaction target of the hydrogenation method of the present invention is a phthalate compound, and hydrogen is added to a benzene ring of the phthalate compound by the hydrogenation, thereby being converted into a cyclohexane dicarboxylate compound corresponding to the phthalate compound.

The phthalate compound may be one or more selected from phthalate, terephthalate, isophthalate, and a carboxylic acid compound corresponding thereto.

First, the phthalate compound may be represented by the following Chemical Formula 1:

[Chemical Formula 1]

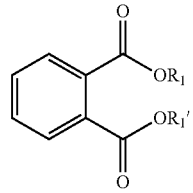

In Chemical Formula 1, R1 and R1' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the phthalate compound may include dibutyl phthalate (DBP), dihexyl phthalate (DHP), dioctyl phthalate (DOP), di-n-octyl phthalate (DnOP), diisononyl phthalate, diisodecyl phthalate (DIDP), etc., but are not limited thereto. These compounds may be used alone or in a mixture.

The terephthalate compound may be represented by the following Chemical Formula 2:

[Chemical Formula 2]

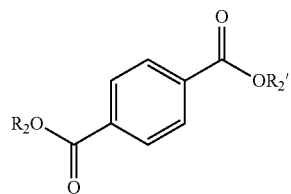

In Chemical Formula 2, R2 and R2' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the terephthalate compound may include dibutyl terephthalate (DBTP), dioctyl terephthalate (DOTP), diisononyl terephthalate (DINTP), or diisodecyl terephthalate (DIDTP), but are not limited thereto. These compounds may be used alone or in a mixture.

The isophthalate compound may be represented by the following Chemical Formula 3:

[Chemical Formula 3]

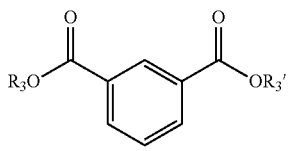

In Chemical Formula 3, R3 and R3' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the isophthalate compound may include dibutyl isophthalate (DBIP), dioctyl isophthalate (DOIP), diisononyl isophthalate (DINIP), diisodecyl isophthalate (DIDIP), etc., but are not limited thereto. These compounds may be used alone or in a mixture.

Preferably, dioctyl terephthalate (DOTP) may be used as the phthalate compound.

Purity of the phthalate compound may be about 99% or more, preferably about 99.5% or more, and more preferably about 98% or more, but is not limited thereto. Any phthalate compound with commercially available quality and purity may be used.

The hydrogenation process of the phthalate compound may be carried out in a liquid phase or in a gas phase. In the present invention, the phthalate compound is included in the liquid-phase raw material and hydrogen is included in the gas-phase raw material, which are introduced into a reactor filled with a hydrogenation catalyst.

In the present invention, the Reynold's number of the liquid-phase raw material introduced into the reactor may be 1 to 100.

The Reynold's number ($N_{RE}$) is a ratio of "inertial forces" to "viscous forces" of a fluid, and represented by the following Equation 1:

$$\text{Reynold's No. } (N_{Re}) = \frac{\rho \times u_z \times D_p}{\mu} \quad \text{[Equation 1]}$$

μ: viscosity ρ: density $u_z$: axial linear velocity $D_p$: diameter of flow path In fluid flow, when viscous forces are greater, a laminar flow occurs, in which elements within the fluid move parallel to each other in the direction of transport, and when inertial forces are greater, a turbulent flow occurs, in which elements within the fluid randomly move in the direction of transport. The Reynold's number is a value used to determine whether a flow in a pipe is a laminar flow or a turbulent flow. When the Reynold's number is about 2000 or less, it is determined as the laminar flow, and when the Reynold's number is more than 2000, it is determined as the turbulent flow. In other words, the lower Reynold's number of the fluid indicates that the flow is steady without turbulence.

In the hydrogenation method of a phthalate compound of the present invention, the Reynold's number of the liquid-phase raw material may be 1 or more, or 5 or more, or 10 or more, or 20 or more, and 100 or less, or 90 or less, or 80 or less, or 50 or less, or 30 or less.

When the Reynold's number of the liquid-phase raw material is as excessively low as less than 1, axial linear velocity is too low or viscosity is too high, and thus distribution of the liquid phase may not normally occur. When the Reynold's number is as excessively high as more than 100, the turbulent flow that randomly moves becomes strong, and with departing from formation of a stable trickle flow, reactivity may be deteriorated. In this point of view, it is preferable that the Reynold's number of the liquid-phase raw material is within the above-described range.

While studying a method of increasing the content of a cis isomer in the product during the hydrogenation process of a phthalate compound, the present inventors found that the Reynold's number of the liquid-phase raw material affects stereoselectivity of the reaction. In other words, as the Reynold's number of the liquid-phase raw material is lower, the content of the cis isomer becomes higher, which is likely to be attributed to an increased rate of concurrent addition of hydrogen to the benzene ring of the phthalate compound due to improved flowability of the raw material on the surface of the catalyst.

In the present invention, the temperature and pressure conditions of the gas-phase raw material and the liquid-phase raw material introduced into the reactor are not particularly limited. However, the raw materials to be introduced may have generally the same pressure as the hydrogenation conditions, and with regard to the temperature condition, the raw materials may have preferably the same temperature as the hydrogenation conditions. Depending on the circumstance, the raw materials having a lower temperature than the hydrogenation conditions may be introduced into the reactor in order to control heat generation in the reactor.

In the present invention, a method of controlling the Reynold's number of the liquid-phase raw material introduced into the reactor is not particularly limited. For example, the Reynold's number of the liquid-phase raw material may be controlled by the temperature, the catalyst size, the reactor diameter, the amount of the liquid-phase raw material passing through the cross-sectional area, etc. In one embodiment of the present invention, the Reynold's number may be controlled by changing the reactor diameter, flow rate, etc., after determining the catalyst size, but the present invention is not limited thereto.

Further, in order to secure the above effects, the amount of hydrogen introduced into the reactor may be 3 mol or more, or 4 mol or more, or 7 mol or more, and 300 mol or less, or 100 mol or less, or 50 mol or less, or 30 mol or less with respect to 1 mol of the phthalate compound. If the amount of hydrogen is as too small as less than 3 mol with respect to 1 mol of the phthalate compound, the reactivity decreases to a level lower than the equivalent ratio. If the amount is as too large as more than 300 mol, the size of the reactor, back-end gas phase process facility, and instrumentation becomes excessively large, and thus the facility costs may increase. In this point of view, it is preferable that the amount of hydrogen is within the above-described range.

The hydrogenation catalyst may include a transition metal as an active ingredient, and may preferably include one or more selected from the group consisting of ruthenium (Ru), palladium (Pd), rhodium (Rh), and platinum (Pt).

The hydrogenation catalyst may be used after being supported on a support. In this regard, as the support, any support known in the art may be used without limitation. Specifically, a support such as zirconia ($ZrO_2$), titania ($TiO_2$), alumina ($Al_2O_3$), silica ($SiO_2$), etc. may be used.

When the hydrogenation catalyst is supported on the support, the amount of the active ingredient of the hydrogenation catalyst may be preferably 3% by weight or less, 2% by weight or less, or 1% by weight or less, and 0.1% by weight or more, or 0.3% by weight or more with respect to 100% by weight of the support. If the amount of the hydrogenation catalyst is more than 3% by weight with respect to 100% by weight of the support, the reaction rapidly occurs on the catalyst surface, and during this process, side reactions also increase, which may cause a problem that the amount of by-products rapidly increases. If the amount is less than 0.1% by weight, the yield of the hydrogenation reaction may decrease due to the insufficient amount of the catalyst. Therefore, the above range is preferred.

In the present invention, the hydrogenation reaction conditions are not particularly limited. However, a reaction pressure may be, for example, 50 bar or more, or 100 bar or more, or 130 bar or more, and 200 bar or less, or 180 bar or less, or 150 bar or less. If the reaction pressure is less than 50 bar, there are various problems in that the solubility of hydrogen in the liquid is too low, and thus reactivity may decrease. If the reaction pressure exceeds 200 bar, the size of the facility may be increased due to high pressure, and thus there is a problem in that the facility costs may be increased. Therefore, the above range is preferred.

Further, the reaction temperature may be 100° C. or higher, or 120° C. or higher, or 130° C. or higher, and 300° C. or lower, or 250° C. or lower, or 200° C. or lower. If the reaction temperature is lower than 100° C., there is a problem in that the reactivity may deteriorate due to the low temperature. If the reaction temperature is higher than 300° C., there is a problem in that by-products are increased due to decomposition, etc.

By the hydrogenation reaction, an aromatic ring of the phthalate compound is hydrogenated to be converted into the cyclohexane dicarboxylate compound corresponding thereto.

After the reaction is terminated, the produced liquid-phase hydrogenation product and unreacted gas-phase raw material are separated from each other. The separated gas-phase raw material may be recirculated in the hydrogenation process. Further, the recovered hydrogenation product may be finally separated through a decompression and cooling process.

According to the hydrogenation method of the present invention, in which the gas-phase and liquid-phase raw materials are introduced into the reactor by controlling their Reynold's number, stereoselectivity of the hydrogenation reaction is improved, and the content of cis isomer in the product is as high as 70% or more, and more preferably 80% or more. As such, as the content of cis isomer is increased, the hydrogenation product prepared by the present invention may exhibit excellent plasticizing efficiency, a high absorption rate, and excellent product transparency after solidification, and has excellent properties as a plastic plasticizer due to low leaching from the product surface even after long-term use thereof.

The drawing illustrates a hydrogenation reaction apparatus used in the hydrogenation method of the present invention. Referring to the drawing, the hydrogenation reaction apparatus may be composed of heat exchangers A and B, a reactor C, and a gas-liquid separator D, etc.

The heat exchangers A and B function to heat a gas-phase raw material 1 and a liquid-phase raw material 3 before introducing them into the reactor C, and may be omitted, as needed.

The gas-phase raw material 2 and the liquid-phase raw material 4 passed through the heat exchangers are introduced into a pipe-type reactor C, of which interior is filled with a hydrogenation catalyst, and the hydrogenation reaction proceeds. The reactor may further include an outer jacket for heat removal in order to control the reaction heat. In this regard, the gas-phase raw material 2 may be fed into an upper portion or a lower portion of the reactor, and the liquid-phase raw material 4 may be fed into the upper portion of the reactor. The liquid raw material flows on the catalyst by gravity from the upper portion to the lower portion of the reactor, and exhibits a trickle flow according to the Reynold's number, and thus hydrogenation proceeds with efficient reactivity.

A reaction mixture 5 discharged from the reactor C is transferred to the gas-liquid separator D, wherein a liquid-phase reaction product 7 and an unreacted gas-phase 6 are separated from each other. The separated reaction product 7 may be recovered and further subjected to a purification process, and the unreacted gas-phase 6 is circulated in order to be discharged or recycled.

However, a position of each of the devices shown in the drawing may be changed, and if necessary, other devices that are not shown in the drawing may be included. Therefore, the hydrogenation method according to the present invention is not limited to the apparatus and the process sequence shown in the drawing.

According to the above-described hydrogenation method of the present invention, stereoselectivity of the hydrogenation reaction is improved, thereby obtaining a reaction product having the cis isomer content of 70% or more. The product exhibits excellent plasticizing efficiency, a high absorption rate, and excellent product transparency after solidification, and has excellent properties as a plastic plasticizer due to low leaching from the product surface even after long-term use thereof.

The hydrogenated phthalate or terephthalate compound prepared as above may be usefully applied as a plasticizer. Specifically, a plasticizer including the phthalate or terephthalate compound may be applied to products such as stabilizers, paints, inks, liquid-phase blowing agents (Masterbatches), adhesives, etc.

The hydrogenated phthalate or terephthalate compound prepared according to the present invention has excellent purity and the high content of cis isomer, and thus its quality as a plasticizer is excellent. Therefore, it may be suitably used as a plasticizer for a resin selected from ethylene vinyl acetate, polyethylene, polypropylene, polyvinyl chloride, polystyrene, polyurethane, polybutadiene, silicone, thermoplastic elastomers, and copolymers thereof.

A resin composition including the phthalate or terephthalate compound prepared according to the present invention as a plasticizer and the above-described resin may be used in a variety of products. For example, the resin composition may be used in the preparation of food packaging film (e.g., wrap), industrial film, compounds, deco sheets, deco tiles, soft sheets, hard sheets, wires and cables, wallpaper, foam mats, leathers, flooring materials, tarpaulin, gloves, sealants, refrigerator gaskets, hoses, medical devices, geogrids, mesh tarpaulins, toys, stationery, insulating tapes, clothing coatings, PVC labels used for clothing or stationery, bottle cap liners, stoppers for industrial or other purposes, artificial baits, parts (e.g., sleeves) in electronic devices, automobile interior materials, adhesives, coating agents, but is not limited thereto.

Hereinafter, actions and effects of the present invention will be described in more detail with reference to specific examples of the present invention. However, these examples

EXAMPLE

Example 1

Dioctyl terephthalate (DOTP) with purity of 99% as a liquid-phase raw material and hydrogen as a gas-phase raw material were introduced into a reactor, and hydrogenation was allowed at a reaction pressure of 150 bar and a reaction temperature of 150° C. At this time, the Reynold's number of the liquid-phase raw material was set to 17.1, followed by operating. Here, the Reynold's number is a value calculated by the following Equation 1:

$$\text{Reynold's No. } (N_{Re}) = \frac{\rho \times u_z \times D_p}{\mu} \quad \text{[Equation 1]}$$

μ: viscosity ρ: density $u_z$: axial linear velocity $D_p$: diameter of catalystflow path The hydrogen and DOTP were introduced at a hydrogen/DOTP molar ratio of 10, and the gas-phase and liquid-phase raw materials were introduced in the same manner as the hydrogenation conditions.

The reactor was in the form of a single tube, and a length of a portion of the tube filled with the catalyst was a total of 3 m. A hydrogenation reaction was performed while circulating the same heating oil as the reaction temperature in the outer jacket.

The catalyst used in the reactor was a ruthenium (Ru) catalyst, which was prepared by using 0.5% by weight of ruthenium with respect to 100% by weight of an alumina support, and the reactor was a cylinder type with a diameter of 3 mm and a height of 3 mm.

Example 2

The hydrogenation reaction was performed in the same manner as in Example 1, except that the Reynold's number of the liquid-phase raw material was 4.9.

Example 3

The hydrogenation reaction was performed in the same manner as in Example 1, except that the Reynold's number of the liquid-phase raw material was 40.3.

Comparative Example 1

The hydrogenation reaction was performed in the same manner as in Example 1, except that the Reynold's number of the liquid-phase raw material was 110.2.

Experimental Example

After the hydrogenation reactions of Examples 1 to 3 and Comparative Example 1 were terminated, unreacted gas-phase raw materials were separated from the reaction mixture to obtain hydrogenation products, respectively. The conversion rates and the contents of cis isomer in the hydrogenation products were measured for Examples and Comparative Example, respectively, and the results are shown in Table 1 below.

TABLE 1

|  | Example 1 | Example 2 | Example 3 | Comparative Example 1 |
|---|---|---|---|---|
| Reynold's number of liquid-phase raw material | 17.1 | 4.9 | 40.3 | 110.2 |
| Catalyst (wt %) | Ru 0.5 | Ru 0.5 | Ru 0.5 | Ru 0.5 |
| Conversion rate (%) | 99.7 | 99.5 | 99.7 | 99.9 |
| Content of cis isomer (%) | 81 | 86.9 | 79.1 | 68.0 |

Referring to Table 1, Examples 1 to 3, in which the process was performed while satisfying the Reynold's number of the present invention, showed the high conversion rate of 99% or more, and the very high content of cis isomer in the hydrogenation product of 79% or more. However, when the process was performed under conditions where the Reynold's number of the liquid-phase raw material did not meet the range of the present invention, the content of cis isomer in the hydrogenation product was remarkably reduced, as in Comparative Example 1.

The above results suggest that, in the hydrogenation method of a phthalate compound, when the Reynold's numbers of the gas-phase and liquid-phase raw materials introduced into the reactor are controlled within the range of the present invention, stereoselectivity of the hydrogenation reaction may be greatly improved, and as a result, the proportion of cis isomer in the hydrogenation product may be remarkably increased. Therefore, it is possible to prepare a hydrogenation product with high quality as a plasticizer.

REFERENCE NUMERALS a, b: Heat exchanger
c: Reactor
d: Gas-liquid separator
1, 2: Gas-phase raw material
3, 4: Liquid-phase raw material
5: Reaction mixture
6: Unreacted gas-phase
7: Liquid-phase reaction product

The invention claimed is:

1. A hydrogenation method of a phthalate compound comprising:
    introducing a gas-phase raw material including hydrogen and a liquid-phase raw material including the phthalate compound into a reactor; and
    performing a reaction of the hydrogen and the phthalate compound in the presence of a hydrogenation catalyst to prepare a hydrogenated phthalate compound,
    wherein the phthalate compound is one or more selected from the group consisting of phthalate, terephthalate and isophthalate,
    an amount of hydrogen introduced into the reactor is 3 mol to 300 mol with respect to 1 mol of the phthalate compound,
    the Reynold's number of the liquid-phase raw material in the reactor is 1 to 100, and
    the content of the cis isomer in the hydrogenated phthalate compound is 70% or more.

2. The hydrogenation method of a phthalate compound of claim 1, wherein the gas-phase raw material is fed into an upper portion or a lower portion of the reactor, and the liquid-phase raw material is fed into an upper portion of the reactor.

3. The hydrogenation method of a phthalate compound of claim 1, wherein the active ingredient of the hydrogenation catalyst is one or more selected from the group consisting of ruthenium (Ru), rhodium (Rh), palladium (Pd), and platinum (Pt).

4. The hydrogenation method of a phthalate compound of claim 1, wherein the hydrogenation catalyst includes 3% by weight or less of the catalyst active ingredient with respect to 100% by weight of a support.

* * * * *